United States Patent
Marušic-Ištuk et al.

(10) Patent No.: US 6,872,707 B1
(45) Date of Patent: Mar. 29, 2005

(54) HALO DERIVATIVES OF 9-DEOXO-9A-AZA-HOMERYTHROMYCIN A

(75) Inventors: Zorica Marušic-Ištuk, Samobor (HR); Nedjelko Kujundžić, Zagreb (HR); Gabrijela Kobrehel, Zagreb (HR); Stjepan Mutak, Zagreb (HR); Nataša Maršić, Zagreb (HR)

(73) Assignee: PLIVA farmaceutska industrija dionicko drustvo, Zagreb (HR)

(*) Notice: Subject to any disclaimer, the term of this patent is extended or adjusted under 35 U.S.C. 154(b) by 0 days.

(21) Appl. No.: 09/959,662
(22) PCT Filed: May 2, 2000
(86) PCT No.: PCT/HR00/00013
§ 371 (c)(1), (2), (4) Date: Nov. 2, 2001
(87) PCT Pub. No.: WO00/66603
PCT Pub. Date: Nov. 9, 2000

(30) Foreign Application Priority Data

May 3, 1999 (HR) .......................... P 990130 A

(51) Int. Cl.[7] ........................ A61K 31/70; C07H 1/00; C07H 17/08
(52) U.S. Cl. ........................ 514/29; 536/7.3; 536/7.4; 536/18.5
(58) Field of Search ............. 514/29; 536/7.3, 536/7.4, 18.5

(56) References Cited

U.S. PATENT DOCUMENTS 5,350,839 A * 9/1994 Asaka et al. ............... 536/7.4
5,629,296 A * 5/1997 Kujund zi c et al. ........ 514/29

* cited by examiner

*Primary Examiner*—Elli Peselev
(74) *Attorney, Agent, or Firm*—Connolly, Bove, Lodge & Hutz, LLP

(57) ABSTRACT

The invention relates to halo derivatives of 9a-N-(N'-arylcarbamoyl)- and 9a-N-(N'-arylthiocarbamoyl)-9-deoxo-9a-aza-9a-homoerythromycin A of the general formula (I)

wherein R has the meaning of a substituted aryl group of the formula (II)

wherein substituents a, b, c, d and e are the same or different and at least one of them has the meaning of halo, a $(C_1-C_6)$haloalkyl or a $(C_1-C_6)$haloalkoxy group, whereas the remaining ones have the meaning of hydrogen, halo, a $(C_1-C_6)$alkyl or a $(C_1-C_6)$alkoxy group, and X has the meaning of oxygen or sulfur, and pharmaceutically acceptable addition salts thereof with inorganic or organic acids, to a process for their preparation, to a process for the preparation of pharmaceutical compositions comprising them and to the use of these pharmaceutical compositions for the treatment or prevention of bacterial infections.

36 Claims, No Drawings

HALO DERIVATIVES OF 9-DEOXO-9A-AZA-HOMERYTHROMYCIN A

1) TECHNICAL FIELD

A 61 K 31/70, C 07 H 17/08

2) TECHNICAL PROBLEM

The invention relates to novel compounds from the class of the macrolide antibiotic erythromycin A. The invention especially relates to halo derivatives of 9a-N-(N'-arylcarbamoyl)- and 9a-N-(N'-arylthiocarbamoyl)-9-deoxo-9a-aza-9a-homoerythromycin A, to pharmaceutically acceptable addition salts thereof with inorganic or organic acids, to a process for their preparation, to pharmaceutical compositions comprising them and to the use of these pharmaceutical compositions for the treatment or prevention of bacterial infections.

3) PRIOR ART

Erythromycin A is a macrolide antibiotic whose structure is characterized by a 14-member lactone ring with C-9 ketone, and two sugars, L-cladinose and D-desosamine, glycosidically bound to C-3 and C-5 positions of an aglycone moiety of the molecule (McGuire, Antiblot. Chemother., 1952; 2:281). By an oximation of C-9 ketone with hydroxylamine-hydrochloride, Beckmann rearrangement of the obtained 9(E)-oxime and reduction of the obtained 6,9-iminoether there is obtained 9-deoxo-9a-aza-9a-homoerythromycin A, the first semisynthetic macrolide with a 15-member azalactone ring (Kobrehel G. et al, U.S. Pat. No. 4,328,334, May 1982).

By selective acylation of 9-deoxo-9a-aza-9a-homoerythromycin A with carboxylic acid anhydrides, corresponding mono-, di-, tri- or tetraacyl derivatives were synthesized and by a transesterification reaction with ethylene carbonate followed by acylation, 11,12-cyclic carbonate and its acyl derivatives were synthesized (Djokić S. et al, J. Antibiotics 40, 1006–1015, 1987).

By reductive methylation of a secondary 9a-amino group of 9-deoxo-9a-aza-9a-homoerythromycin A according to Eschweiler-Clark process, 9-deoxo-9a-methyl-9a-aza-9a-homoerythromycin A (azithromycin), a prototype of a novel class of 9a-azalide antibiotics (Kobrehel G. et al, BE 892 357, July 1982) was synthesized. In addition to a broad antimicrobial spectrum also including Gram negative bacteria, azithromycin is characterized by a long biological half-life, a specific mechanism of transport to the application site and a short therapy period. Azithromycin easily penetrates and is accumulated inside human phagocyte cells resulting in an improved action with regard to intracellular pathogenic microorganisms of the classes *Legionella, Chlamydia* and *Helicobacter*. Bright G. M. et al (J. Antibiotics 41, 1092–1047, 1987) synthesized a series of 9-a-N-alkyl analogues of azithromycin, disclosed the epimerization of the 4"-hydroxyl group and the preparation of a corresponding 4"-amino derivative.

The synthesis and antibacterial activity of 9a, 11-cyclic ethers of 9-deoxo-9a-aza-9a-homoerythromycin A are disclosed in U.S. Pat. No. 4,492,688, January 1985 (Bright G. M.). The preparation and activity spectrum of 9a,11-cyclic carbamate of 9-deoxo-9a-aza-11-deoxy-9a-homoerythromycin A and its O-methyl derivatives are disclosed in U.S. Pat. No. 5,434,140, July 1995 (Kobrehel G. et al).

Recently, Blizzard T. A. et al (WO 99/00125, July 1998) disclosed novel 9a-N,6-O-methylene-9-deoxo-9a-aza-9a-homoerythromycin A derivatives and corresponding 9a-N,6-O-carbamates as intermediates in the synthesis of 3-keto derivatives from the class of 9a-azalides.

It has also been disclosed that by a reaction of 9-deoxo-9a-aza-9a-homoerythromycin A with isocyanates or isothiocyanates, corresponding 9a-N-(N'-carbamoyl)- and 9a-N-(N'-thiocarbamoyl) derivatives may be prepared (Kujundžić N. et al, U.S. Pat. No. 5,629,296, May 1997). This invention relates to N'-($C_1$–$C_3$)alkylcarbamoyl, N'-arylcarbamoyl and N'-aralkylcarbamoyl derivatives and to thiocarbamoyl analogues thereof, resp. Although the antibacterial spectrum of these 9a-azalides is similar to the action of azithromycin, the effectiveness is 2 to 8 times smaller, even in case of the most active representatives (N'-naphthylcarbamoyl and N'-benzylthiocarbamoyl derivatives).

According to the well-known and established Prior Art, halo derivatives of 9a-N-(N'-arylcarbamoyl)- and 9a-N-(N'-arylthiocarbamoyl)-9-deoxo-9a-aza-9a-homoerythromycin A, which are the object of the present invention, pharmaceutically acceptable addition salts thereof with inorganic or organic acids, a process for the preparation thereof, a process for the preparation of pharmaceutical compositions comprising them and the use of these pharmaceutical compositions for the treatment or prevention of bacterial infections have not been disclosed so far.

The object of the present invention is the preparation of novel 9a-N-(N'-arylcarbamoyl)- and 9a-N-(N'-arylthiocarbamoyl)-9-deoxo-9a-aza-9a-homoerythromycins A wherein at least one of the substituents on the aromatic ring has the meaning of halo, a ($C_1$–$C_6$)haloalkyl or a ($C_1$–$C_6$)haloalkoxy group. Novel 9a-azalides of the present invention are characterized by a broad antibacterial spectrum of action including an action upon sensitive and resistent Gram positive and Gram negative microorganisms.

4) THE INVENTIVE SOLUTION

It has been found that halo derivatives of 9a-N-(N'-arylcarbamoyl)- and 9a-N-(N'-arylthiocarbamoyl)-9-deoxo-9a-aza-9a-homoerythromycin A of the general formula (I)

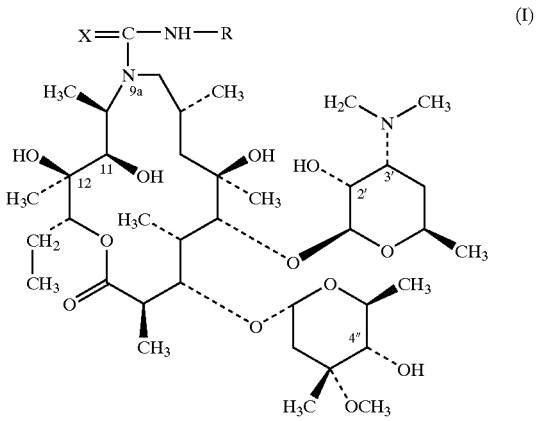

(I)

wherein R has the meaning of a substituted aryl group of the formula (II)

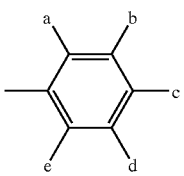
(II)

wherein substituents a, b, c, d and e are the same or different and at least one of them has the meaning of halo, a ($C_1$–$C_6$)haloalkyl or a ($C_1$–$C_6$)haloalkoxy group whereas the remaining ones have the meaning of hydrogen, halo, a ($C_1$–$C_6$)alkyl or a ($C_1$–$C_6$)alkoxy group, and X has the meaning of oxygen or sulfur, and pharmaceutically acceptable addition salts thereof with inorganic or organic acids, may be prepared by the reaction of 9-deoxo-9a-aza-9a-homoerythromycin A with isocyanates or isothiocyanates of the general formula (III)

(III)

wherein R and X have the above meanings, in an aprotic solvent, preferably toluene, at room temperature or at elevated temperature. After the completed reaction the product is isolated by evaporation under reduced pressure and optionally by the use of standard techniques such as chromatography on a silica gel column or recrystallization.

Further, an object of the invention are pharmaceutically acceptable addition salts which, according to recognized medical practice, are non-toxic and in contact with human tissues or tissues of lower mammals do not induce irritation or allergic reactions. The term "pharmaceutically acceptable salts" relates to addition salts of compounds of the general formula (I) with non-toxic inorganic or organic acids. They are prepared in situ in the course of isolation or purification of compounds of the invention or subsequently by the reaction of the 3'-dimethylamino group of the isolated base with an at least equimolar amount of the appropriate inorganic or organic acid. Suitable inorganic acids are e.g. hydrochloric, hydrobromic, hydroiodic, sulfuric, phosphoric or perchloric acid and organic acids are acetic, trifluoroacetic, propionic, benzoic, benzenesulfonic, methanesulfonic, laurylsulfonic, adipic, ascorbic, camphoric, gluconic, fumaric, stearic, palmitic, succinic, ethylsuccinic, lactobionic, oxalic, salicylic acid and similar acids. The reaction of the base with appropriate acids is carried out in an inert solvent and addition salts are isolated by evaporation of solvents or, alternatively, by filtration after a spontaneous precipitation or after precipitation with the addition of a non-polar co-solvent.

Novel halo derivatives of 9a-N-(N'-arylcarbamoyl)- and 9a-N-(N'-arylthiocarbamoyl)-9-deoxo-9a-aza-9a-homoerythromycin A of the general formula (I) and pharmaceutically acceptable addition salts thereof with inorganic or organic acids possess an effective antibacterial activity. In vitro action of the novel compounds was investigated on a series of standard and resistent test microorganisms. Generally, it was demonstrated by investigating the effectiveness of haloaryl derivatives upon S. aureus, E. faecalis and S. pneumoniae that 9a-N-(N'-thiocarbamoyl) derivatives were more active than 9a-N-(N-carbamoyl) derivatives. N'-fluoroaryl derivatives were the most active ones in the series. The position of the substitution did not affect the activity, however, haloarylcarbamoyl derivatives substituted in 2-position were shown to have the best antibacterial in vitro activity. In N'-($C_1$–$C_6$)haloalkylcarbamoyl derivatives similar traits were observed.

However, in the series of thiocarbamoyl analogues, N'-(3-trifluoromethyl) arylthiocarbamoyl derivative was shown to be the most active one and, in addition to the activity against test microorganisms sensitive to erythromycin, it also showed an activity against resistent strains.

The object of the present invention are also pharmaceutical compositions comprising a therapeutically effective amount of the compounds of the general formula (I) and one or more non-toxic pharmaceutically acceptable carriers. The term "pharmaceutically acceptable carrier" means a non-toxic inert solid, semisolid, liquid filler, diluent etc. Materials that may serve as pharmaceutically acceptable carriers are sugars e.g. lactose, glucose or saccharose, starch, cellulose and its derivatives, e.g. carboxymethyl cellulose or ethyl cellulose, then gelatine, talc, arachis oil, sesame oil, soya-bean oil, glycols e.g. propylene glycol, esters e.g. ethyl acetate or ethyl laurate, agar, buffering agents e.g. magnesium hydroxide or aluminum hydroxide, pyrogen-free water, isotonic solution, Ringer solution, ethanol, phosphate buffer, fragrances, colouring agents, sweeteners etc.

Pharmaceutical compositions of the present invention may be administered orally, parenterally, intravaginally, rectally or intraperitoneally to humans and animals. Liquid formulations for oral application include pharmaceutically acceptable emulsions, microemulsions, solutions, suspensions, syrups and elixirs. In addition to an active component, the liquid formulations may also contain inert diluents e.g. water or other solvents, and various additives. Injection forms e.g. sterile aqueous suspensions are formulated according to well-known processes.

A further object of the invention is a method for the treatment or prevention of bacterial infections in humans and animals, which, in case of need or prophylaxis, includes the application of a therapeutically effective amount of the compound of the general formula (I) for a period of time necessary to achieve a therapeutical action. "A therapeutically effective amount" means a sufficient amount of a substance for the treatment of a bacterial infection in any medical application while carefully observing the interaction of usefulness and risk. The total amount of a daily dosis of compounds of the present invention in applications to humans or animals in a single or a multiple dosis is in the range of from 0.001 to 50 mg/kg of body weight. Generally, the treatment regimen according to the present invention includes, in case of need, an administration of 10 to 100 mg/day of the compound of the general formula (I) in a single or multiple dosis.

The process for the preparation of halo derivatives of 9a-N-(N'-arylcarbamoyl)- and 9a-N-(N'-arylthiocarbamoyl)-9-deoxo-9a-aza-9a-homoerythromycin A of the present invention is illustrated by the following Examples which should in no way be construed as a limitation thereof.

EXAMPLE 1

9-deoxo-9a-N-{N'-[(2-fluoro-phenyl)carbamoyl]}-9a-aza-9a-homoerythromycin A

From 9-deoxo-9a-aza-9a-homoerythromycin A (3.0 g; 0.00408 mole), 2-fluorophenyl-isocyanate (0.61 g; 0.00448 mole) and toluene (40 ml) under stirring for 1 hour at room temperature and by evaporation of the reaction mixture under reduced pressure a crude product (3.81 g) was obtained. By crystallization from a diethyl ether-petroleum ether mixture a chromatographically homogeneous title product (2.74 g) having the following physico-chemical constants was obtained:

M.p. 129–132° C.

IR (KBr) cm$^{-1}$ 3468, 2973, 2937, 1732, 1668, 1619, 1533, 1455, 1380, 1324, 1253, 1167, 1094, 1054, 1013, 958, 897, 834, 753.

FAB-MS 872 [MH$^+$]

EXAMPLE 2

9-deoxo-9a-N-{N'-[(2-fluoro-phenyl)thiocarbamoyl]}-9a-aza-9a-homoerythromycin A

From 9-deoxo-9a-aza-9a-homoerythromycin A (3.0 g; 0.00408 mole), 2-fluorophenyl-isothiocyanate (0.69 g; 0.00448 mole) and toluene (40 ml) under stirring for 12 hours at room temperature and by evaporation of the reaction mixture under reduced pressure a crude product (3.45 g) was obtained. By crystallization from an acetone-petroleum ether mixture a chromatographically homogeneous product (2.05 g) having the following physico-chemical constants was obtained:

IR (KBr) cm$^{-1}$ 3431, 2971, 2936, 1729, 1620, 1514, 1457, 1380, 1314, 1280, 1167, 1094, 1052, 1012, 958, 896, 831, 756.

FAB-MS 888 [MH$^+$]

EXAMPLE 3

9-deoxo-9a-N-{N'-[(2-chloro-phenyl)thiocarbamoyl]}-9a-aza-9a-homoerythromycin A

From 9-deoxo-9a-aza-9a-homoerythromycin A (3.0 g; 0.00408 mole), 2-chlorophenyl-isothiocyanate (0.76 g; 0.00448 mole) and toluene (40 ml) under stirring for 12 hours at the temperature of 40° C. and by evaporation of the reaction mixture under reduced pressure a crude product (3.51 g) was obtained. By crystallization from an acetone-petroleum ether mixture a chromatographically homogeneous product (2.24 g) having the following physico-chemical constants was obtained:

IR (KBr) cm$^{-1}$ 3411, 2972, 2937, 2058, 1726, 1593, 1520, 1494, 1456, 1379, 1310, 1244, 1168, 1093, 1054, 1014, 958, 897, 834, 754, 735.

FAB-MS 904 [MH$^+$]

EXAMPLE 4

9-deoxo-9a-N-{N'-[(2-chloro-6-methyl-phenyl)carbamoyl]}-9a-aza-9a-homoerythromycin A From 9-deoxo-9a-aza-9a-homoerythromycin A (1.5 g; 0.00204 mole), 2-chloro-6-methyl-phenylisocyanate (0.37 g; 0.00228 mole) and toluene (15 ml) under stirring for 1 hour at room temperature and by evaporation of the reaction mixture under reduced pressure a crude product (1.85 g) was obtained. By chromatography on a silica gel column using the solvent system methylene chloride-methanol 90:5, a chromatographically homogeneous product (1.36 g) having the following physico-chemical constants was obtained:

IR (KBr) cm$^{-1}$ 3437, 2973, 2937, 1732, 1645, 1595, 1510, 1456, 1379, 1280, 1167, 1010, 1053, 1014, 959, 897, 864, 835, 771.

EXAMPLE 5

9-deoxo-9a-N-{N'-[(3-fluoro-phenyl)carbamoyl]}-9a-aza-9a-homoerythromycin A

From 9-deoxo-9a-aza-9a-homoerythromycin A (3.0 g; 0.00408 mole), 3-fluorophenyl-isocyanate (0.61 g; 0.00448 mole) and toluene (40 ml) under stirring for 1 hour at room temperature and by evaporation of the reaction mixture under reduced pressure a crude product (3.60 g) was obtained. By crystallization from an acetone-petroleum ether mixture a chromatographically homogeneous product (2.64 g) having the following physico-chemical constants was obtained:

M.p. 140–143° C.

IR (KBr) cm$^{-1}$ 3454, 2975, 2939, 1712, 1651, 1602, 1537, 1494, 1443, 1380, 1317, 1278, 1247, 1167, 1053, 1013, 959, 896, 865, 835, 772, 681.

FAB-MS 872 [MH$^+$]

EXAMPLE 6

9-deoxo-9a-N-{N'-[(3-chloro-phenyl)carbamoyl]}-9a-aza-9a-homoerythromycin A

From 9-deoxo-9a-aza-9a-homoerythromycin A (3.0 g; 0.00408 mole), 3-chlorophenyl-isocyanate (0.68 g; 0.00448 mole) and toluene (40 ml) under stirring for 1 hour at room temperature and by evaporation of the reaction mixture under reduced pressure a crude product (3.52 g) was obtained. By crystallization from diethyl ether a chromatographically homogeneous product (1.29 g) having the following physico-chemical constants was obtained:

IR (KBr) cm$^{-1}$ 3452, 2974, 2939, 2787, 1731, 1669, 1592, 1526, 1484, 1456, 1423, 1380, 1300, 1274, 1246, 1167, 1110, 1013, 958, 897, 834, 775, 681.

$^1$H NMR (300 MHz, CDCl$_3$) δ 7.44–6.94 (Ph), 4.93 (H-13), 4.81 (H-1''), 4.42 (H-1'), 4.06 (H-5''), 4.04 (H-3), 3.90 (H-11), 3.83 (H-9a), 3.56 (H-5'), 3.51 (H-5), 3.32 (H-2'), 3.28 (3''-OCH$_3$), 2.96 (H-4''), 2.70 (H-2), 2.59 (H-3'), 2.46 (H-9b), 2.38 (H-8), 2.36 (3'-N(CH$_3$)$_2$), 2.30 (H-2''a), 1.94 (H-14a), 1.89 (H-4), 1.72 (H-4'), 1.58 (H-14b), 1.54 (H-2''b), 1.42 (10-CH$_3$), 1.27 (2-CH$_3$), 1.23 (5''-CH$_3$), 1.21 (3''-CH$_3$), 1.19 (10-CH$_3$), 1.17 (12-CH$_3$), 1.15 (5'-CH$_3$), 1.07 (4-CH$_3$), 1.07 (8-CH$_3$), 0.93 (15-CH$_3$).

$^{13}$C NMR (75 MHz, CDCl$_3$) δ 157.0 (9a-NCONH), 176.8 (C-1), 140.5, 134.2, 129.5, 122.4, 119.5, 117.5 (Ph), 104.4 (C-1'), 95.9 (C-1''), 87.8 (C-5). 79.2 (C-3), 78.2 (C-13), 77.4 (C-4''), 74.7 (C-11), 74.5, 74.4 (C-6 and C-12), 72.5 (C-3''), 70.5 (C-2'), 69.1 (C-5'), 65.8 (C-5''), 64.5 (C-3'), 49.1 (3''-OCH$_3$), 46.3 (C-2), 41.2 (C-4), 40.1 [3'-N(CH$_3$)$_2$], 34.7 (C-2''), 29.0 (C-4'), 27.2 (C-8), 21.8 (C-14), 21.3 (8-CH$_3$), 20.8 (5'-CH$_3$), 21.1 (3''-CH$_3$), 17.5 (5''-CH$_3$), 17.0 (12-CH$_3$), 15.1 (2-CH$_3$), 13.1 (10-CH$_3$), 11.0 (15-CH$_3$), 9.8 (4-CH$_3$).

EXAMPLE 7

9-deoxo-9a-N-{N'-[(3-bromo-phenyl)carbamoyl]}-9a-aza-9a-homoerythromycin A

From 9-deoxo-9a-aza-9a-homoerythromycin A (1.5 g; 0.00204 mole), 3-bromophenyl-isocyanate (0.44 g; 0.00228 mole) and toluene (20 ml) under stirring for 1 hour at room temperature and by evaporation of the reaction mixture under reduced pressure a crude product (1.94 g) was obtained. By crystallization from an acetone-petroleum ether mixture a chromatographically homogeneous product having the following physico-chemical constants was obtained:

IR(KBr) cm$^{-1}$ 3446, 3291, 2974, 2936, 1727, 1638, 1582, 1546, 1475, 1418, 1402, 1381, 1312, 1286, 1226, 1167, 1066, 995, 874, 855, 788, 774, 745, 685, 641.

FAB-MS [MH$^+$]

EXAMPLE 8

9-deoxo-9a-N-{N'-[(3-fluoro-phenyl)thiocarbamoyl]}-9a-aza-9a-homoerythromycin A

From 9-deoxo-9a-aza-9a-homoerythromycin A (3.0 g; 0.00408 mole), 3-fluorophenyl-isothiocyanate (0.6 g; 0.00448 mole) and toluene (40 ml) under stirring for 24 hours at the temperature of 50° C. and by evaporation of the reaction mixture under reduced pressure a crude product (3.25 g) was obtained. By chromatography on a silica gel column using the solvent system methylene chloride-methanol 9:1, a chromatographically homogeneous product (1.08 g) having the following physico-chemical constants was obtained:

IR(KBr) cm$^{-1}$ 3435, 2971, 2937, 1728, 1712, 1611, 1515, 1493, 1456, 1379, 1313, 1279, 1168, 1093, 1052, 1011, 959, 896, 832, 778, 727, 636.

FAB-MS 888 [MH$^-$]

EXAMPLE 9
9-deoxo-9a-N-{N'-[(3-chloro-phenyl)thiocarbamoyl]}-9a-aza-9a-homoerythromycin A From 9-deoxo-9a-aza-9a-homoerythromycin A (3.0 g; 0.00408 mole), 3-chlorophenyl-isothiocyanate (0.76 g; 0.00448 mole) and toluene (40 ml) under stirring for 24 hours at the temperature of 40° C. and by evaporation of the reaction mixture under reduced pressure a crude product (3.51 g) was obtained. By crystallization from diethyl ether a chromatographically homogeneous product (2.25 g) having the following physico-chemical constants was obtained:

IR (KBr) cm$^{-1}$ 3436, 2974, 2938, 1712, 1683, 1594, 1483, 1460, 1424, 1378, 1308, 1167, 1092, 1053, 1014, 958, 896, 835, 782, 727.

$^1$H NMR (300 MHz, CDCl$_3$) δ 7.47–7.12 (Ph), 4.85 (H-1"), 4.81 (H-13), 4.42 (H-1'), 4.11 (H-3), 4.08 (H-5"), 3.50 (H-5'), 3.48 (H-5), 3.29 (3"-OCH$_3$), 3.25 (H-2'), 3.04 (H-9a), 3.02 (H-4"), 2.80 (H-2), 2.64 (H-10), 2.54 (H-3'), 2.35 (H-2"a), 2.30 (3'-N(CH$_3$)$_2$), 1.88 (H-4), 1.78 (H-8), 1.69 (H-4'), 1.29 1.58 (H-14b), 1.56 (H-2"b), 1.32 (6-CH$_3$), 1.29 (5"-CH$_3$), 1.29 (12-CH$_3$), 1:21 (5'-CH$_3$), 1.21 (2-CH$_3$), 1.19 (10-CH$_3$), 1.09 (4-CH$_3$), 1.08 (3"-CH$_3$), 0.95 (8-CH$_3$), 0.91 (15-CH$_3$).

$^{13}$C NMR (75 MHz, CDCl$_3$) δ 183.2 (9a-NSONH), 177.8 (C-1), 141.1, 133.6, 131.0, 129.3, 127.4, 125.7, 123.68 (Ph), 103.8 (C-1'), 95.1 (C-1"), 86.1 (C-5), 79.5 (C-3), 77.9 (C-13), 77.6 (C-4"), 72.4 (C-3"), 70.6 (C-2'), 68.9 (C-5'), 65.4 (C-5"), 64.9 (C-3'), 56.7 (C-9), 56.5 (C-10), 49.2 (3"-OCH$_3$), 44.9 (C-2), 41.8 (C-7), 41.3 (C-4), 40.2 [3'-N(CH$_3$)$_2$], 34.7 (C-2"), 29.3 (C-8), 28.9 (C-4'), 27.0 (6-CH$_3$), 21.7 (C-14), 21.3 (8-CH$_3$), 21.2 (5'-CH$_3$), 21.0 (3"-CH$_3$), 18.1 (5"-CH$_3$), 16.9 (12-CH$_3$), 15.7 (2-CH$_3$), 14.9 (10-CH$_3$), 11.0 (15-CH$_3$), 9.5 (4-CH$_3$).

FAB-MS 904 [MH$^+$]

EXAMPLE 10
9-deoxo-9a-N-{N'-[(3-bromo-phenyl)thiocarbamoyl]}-9a-aza-9a-homoerythromycin A From 9-deoxo-9a-aza-9a-homoerythromycin A (1.5 g; 0.00204 mole), 97% 3-bromophenylisothiocyanate (0.49 g; 0.00228 mole) and toluene (20 ml) under stirring for 24 hours at the temperature of 60° C. and by evaporation of the reaction mixture under reduced pressure a crude product (1.92 g) was obtained. By crystallization from the system acetone-petroleum ether a chromatographically homogeneous product (0.99 g) having the following physico-chemical constants was obtained:

IR (KBr) cm$^{-1}$ 3434, 2970, 2936, 2024, 1730, 1591, 1456, 1379, 1310, 1167, 1093, 1052, 1012, 958, 896, 832, 777, 730, 636.

FAB-MS 948 [MH$^+$]

EXAMPLE 11
9-deoxo-9a-N-{N'-[(4-chloro-phenyl)carbamoyl]}-9a-aza-9a-homoerythromycin A From 9-deoxo-9a-aza-9a-homoerythromycin A (3.0 g; 0.00408 mole), 4-chlorophenyl-isocyanate (0.68 g; 0.00448 mole) and toluene (40 ml) under stirring for 1 hour at room temperature and by evaporation of the reaction mixture under reduced pressure a crude product (3.54 g) was obtained. By crystallization from hot acetone a chromatographically homogeneous product (2.16 g) having the following physico-chemical constants was obtained:

IR (KBr) cm$^{-1}$ 3444, 2975, 2938, 1713, 1651, 1593, 1520, 1495, 1457, 1379, 1305, 1244, 1166, 1092, 1053, 1013, 959, 896, 829, 755.

FAB-MS 888.4 [MH$^+$]

EXAMPLE 12
9-deoxo-9a-N-{N'-[(4-bromo-phenyl)carbamoyl]}-9a-aza-9a-homoerythromycin A From 9-deoxo-9a-aza-9a-homoerythromycin A (3.0 g; 0.00408 mole), 4-bromophenyl-isocyanate (0.89 g; 0.00448 mole) and toluene (40 ml) under stirring for 1 hour at room temperature and by evaporation of the reaction mixture under reduced pressure a crude product (4.30 g) was obtained. By crystallization from an acetone-petroleum ether mixture a chromatographically homogeneous product (2.20 g) having the following physico-chemical constants was obtained:

IR (KBr) cm$^{-1}$ 3531, 3438, 2977, 2938, 1708, 1683, 1651, 1589, 1520, 1492, 1460, 1377, 1305, 1287, 1244, 1165, 1092, 1053, 1012, 959, 864, 825, 755, 731, 639.

FAB-MS 932 [MH$^+$]

EXAMPLE 13
9-deoxo-9a-N-{N'-[(4-chloro-phenyl)thiocarbamoyl]}-9a-aza-9a-homoerythromycin A From 9-deoxo-9a-aza-9a-homoerythromycin A (3.0 g; 0.00408 mole), 4-chlorophenyl-isothiocyanate (0.76 g; 0.00448 mole) and toluene (40 ml) under stirring for 1 hour at room temperature and by evaporation of the reaction mixture under reduced pressure a crude product (3.71 g) was obtained. By crystallization from hot acetone a chromatographically homogeneous product (3.26 g) having the following physico-chemical constants was obtained:

IR (KBr) cm$^1$ 3534, 3422, 2978, 2939, 2879, 1699, 1683, 1651, 1586, 1530, 1495, 1461, 1409, 1378, 1310, 1279, 1260, 1229, 1167, 1094, 1052, 1012, 952, 894, 865, 833, 727.

FAB-MS 904 [MH$^+$]

EXAMPLE 14
9-deoxo-9a-N-{N'-[(4-bromo-phenyl)thiocarbamoyl]}-9a-aza-9a-homoerythromycin A From 9-deoxo-9a-aza-9a-homoerythromycin A (1.5 g; 0.00204 mole), 4-bromophenyl-isothiocyanate (0.47 g; 0.00228 mole) and toluene (25 ml) under stirring for 12 hours at the temperature of 50° C. and by evaporation of the reaction mixture under reduced pressure a crude product (2.01 g) was obtained. By crystallization from an acetone-petroleum ether mixture a chromatographically homogeneous product (1.92 g) having the following physico-chemical constants was obtained:

IR (KBr) cm$^{-1}$ 3533, 3433, 2974, 2937, 2878, 2786, 1703, 1682, 1626, 1588, 1526, 1492, 1460, 1377, 1312, 1282, 1166, 1093, 1053, 1011, 958, 895, 864, 831, 730.

FAB-MS 948 [MH$^+$]

EXAMPLE 15
9-deoxo-9a-N-{N'-[(3-fluoromethyl-4-chloro-phenyl)carbamoyl]}-9a-aza-9a-homoerythromycin A From 9-deoxo-9a-aza-9a-homoerythromycin A (1.5 g; 0.00204 mole), 3-fluoromethyl-4-chlorophenylisocyanate (0.50 g; 0.00228 mole) and toluene (15 ml) under stirring for 1 hour at room temperature and by evaporation of the reaction mixture under reduced pressure a product (1.99 g) was obtained. By crystallization from an ethyl acetate-(n-hexane) mixture a chromatographically homogeneous product (1.28 g) having the following physico-chemical constants was obtained:

IR (KBr) cm$^{-1}$ 3444, 2976, 2940, 1732, 1713, 1663, 1531, 1486, 1456, 1417, 1380, 1325, 1263, 1168, 1135, 1112, 1093, 1053, 1031, 1012, 958, 896, 830.

FAB-MS 956.5 [MH$^+$]

EXAMPLE 16

9-deoxo-9a-N-{N'-[(2,4-dichloro-phenyl)carbamoyl]}-9a-aza-9a-homoerythromycin A

From 9-deoxo-9a-aza-9a-homoerythromycin A (1.5 g; 0.00204 mole), 2,4-dichloro-phenylisocyanate (0.41 g; 0.00228 mole) and toluene (15 ml) under stirring for 3 hours at room temperature and by evaporation of the reaction mixture under reduced pressure a crude product (1.89 g) was obtained. By crystallization from an ethyl acetate-(n-hexane) mixture a chromatographically homogeneous product (1.14 g) having the following physico-chemical constants was obtained:

IR (KBr) cm$^{-1}$ 3438, 2976, 2939, 1732, 1670, 1651, 1582, 1514, 1487, 1464, 1409, 1381, 1300, 1167, 1053, 1015, 959, 895, 863, 820, 760.

FAB-MS 922.4 [MH$^+$]

EXAMPLE 17

9-deoxo-9a-N-{N'-[(2,4-dichloro-phenyl)thiocarbamoyl]}-9a-aza-9a-homoerythromycin A From 9-deoxo-9a-aza-9a-homoerythromycin A (1.5 g; 0.00204 mole), 2,4-dichloro-phenylisothiocyanate (0.45 g; 0.00228 mole) and toluene (15 ml) under stirring for 7 hours at room temperature and by evaporation of the reaction mixture under reduced pressure a crude product (1.96 g) was obtained. By crystallization from an ethyl acetate-(n-hexane) mixture a chromatographically homogeneous product (1.22 g) having the following physico-chemical constants was obtained:

IR (KBr) cm$^{-1}$ 3425, 2975, 2936, 1737, 1590, 1505, 1460, 1379, 1311, 1166, 1092, 1051, 1013, 956, 903, 864, 834, 759, 730.

FAB-MS 938.4 [MH$^+$]

EXAMPLE 18

9-deoxo-9a-N-{N'-[(2-trifluoromethyl-phenyl)carbamoyl]}-9a-aza-9a-homoerythromycin A From 9-deoxo-9a-aza-9a-homoerythromycin A (1.5 g; 0.00204 mole), 2-trifluoro-methylphenylisocyanate (0.43 g; 0.0023 mole) and toluene (15 ml) under stirring for 7 hours at room temperature and by evaporation of the reaction mixture under reduced pressure a crude product (1.96 g) was obtained. By crystallization from an ethyl acetate-(n-hexane) mixture a chromatographically homogeneous product (1.22 g) having the following physico-chemical constants was obtained:

$^1$H NMR (300 MHz, CDCl$_3$) δ 8.06 (9a-NCONH), 7.57–7.10 (Ph), 5.04 (H-13), 4.82 (H-1"), 4.41 (H-1'), 4.07 (H-5"), 4.05 (H-3), 3.87 (H-11), 3.63 (H-5'), 3.49 (H-5), 3.32 (H-2'), 3.27 (3"-OCH$_3$), 2.97 (H-4"), 2.68 (H-2), 2.61 (H-3'), 2.38 (H-8), 2.33 (3'-N(CH$_3$)$_2$), 2.31 (H-2"a), 1.94 (H-14a), 1.92 (H-4), 1.70 (H-4'), 1.54 (H-2"b), 1.50 (H-14b), 1.39 (10-CH$_3$), 1.31 (2-CH$_3$), 1.26 (5"-CH$_3$), 1.25* (3"-CH$_3$), 1.22* (12-CH$_3$), 1.18 (5'-CH$_3$), 1.06 (4-CH$_3$), 1.06 (8-CH$_3$), 0.92 (15-CH$_3$).

$^{13}$C NMR (75 MHz, CDCl$_3$) δ 156.8 (9a-NCONH), 176.1 (C-1), 136.7, 132.6, 125.8, 124.4, 123.1 (Ph), 129.7, 126.1, 122.5, 118.9 (CF$_3$), 104.8 (C-1'), 97.2 (C-1"), 83.2 (C-5), 79.3 (C-3), 77.4 (C-13), 77.9 (C-4"), 74.1 (C-11), 72.5 (C-3"), 70.5 (C-2'), 69.1 (C-5'), 66.0 (C-5"), 64.5 (C-3'), 49.2 (3"-OCH$_3$), 46.8 (C-2), 41.1 (C-4), 40.2 [3'-N(CH$_3$)$_2$], 34.8 (C-2"), 29.4 (C-4'), 27.4 (C-8), 21.9 (C-14), 20.6 (8-CH$_3$), 21.2 (5'-CH$_3$), 20.7 (3"-CH$_3$), 17.6 (5"-CH$_3$), 17.0 (12-CH$_3$), 15.5 (2-CH$_3$), 12.7 (10-CH$_3$), 11.1 (15-CH$_3$), 10.2 (4-CH$_3$).

FAB-MS 922.3 [MH$^+$]

EXAMPLE 19

9-deoxo-9a-N-{N'-[(3-trifluoromethyl-phenyl)carbamoyl]}-9a-aza-9a-homoerythromycin A From 9-deoxo-9a-aza-9a-homoerythromycin A (7.27 g; 0.00989 mole), 3-trifluoro-methylphenylisocyanate (2.43 g; 0.01298 mole) and toluene (40 ml) under stirring for 1 hour at room temperature and by evaporation of the reaction mixture under reduced pressure a crude product (10.51 g) was obtained. By chromatography on a silica gel column using the system methylene chloride-methanol-conc. ammonia 9:9:1.5, a product (4.1 g) was obtained, which after crystallization from a diethyl ether-petroleum ether mixture had the following physico-chemical constants:

M.p. 122–125° C.

IR (KBr) cm$^{-1}$ 3444, 2974, 2939, 1733, 1651, 1544, 1494, 1447, 1380, 1259, 1166, 1125, 1093, 1070, 1053, 1014, 957, 897, 834, 795, 699.

FAB-MS 922.4 [MH$^+$]

EXAMPLE 20

9-deoxo-9a-N-{(N'-[(4-trifluoromethyl-phenyl)carbamoyl]}-9a-aza-9a-homoerythromycin A From 9-deoxo-9a-aza-9a-homoerythromycin A (3.0 g; 0.00408 mole), 4-trifluoro-methylphenylisocyanate (0.84 g; 0.00448 mole) and toluene (40 ml) under stirring for 1 hour at room temperature and by evaporation of the reaction mixture under reduced pressure a precipitate (3.75 g) was obtained. By crystallization from an ethyl acetate-(n-hexane) mixture, from the crude product (1.2 g) the title product (0.99 g) having the following physico-chemical constants was obtained:

IR (KBr) cm$^{-1}$ 3445, 2974, 2939, 1731, 1668, 1602, 1526, 1457, 1413, 1380, 1325, 1249, 1166, 1115, 1068, 1054, 1015, 959, 897, 838.

$^1$H NMR (300 MHz, CDCl$_3$) δ 8.25 (9a-NCONH), 7:65–7.20 (Ph), 4.91 (H-13), 4.82 (H-1"), 4.41 (H-1'), 4.03 (H-5"), 4.06 (H-3), 3.91 (H-11), 3.51 (H-5'), 3.54 (H-5), 3.30(H-2'), 3.28 (3"-OCH$_3$), 2.97 (H-4"), 2.71 (H-2), 2.55 (H-3'), 2.39 (H-8), 2.31 (3'-N(CH$_3$)$_2$), 2.31 (H-2"a), 1.94 (H-14a), 1.88 (H-4), 1.68 (H-4'), 1.55 (H-2"b), 1.56 (H-14b), 1.45 (10-CH$_3$), 1.26 (2-CH$_3$), 1.21 (5"-CH$_3$), 1.21 (3"-CH$_3$), 1.19 (12-CH$_3$), 1.11 (5'-CH$_3$), 1.07 (4-CH$_3$), 1.08 (8-CH$_3$), 0.93 (15-CH$_3$).

$^{13}$C NMR (75 MHz, CDCl$_3$) δ 156.9 (9a-NCONH), 171.0 (C-1), 142.6, 125.8, 118.9 (Ph), 124.2, 123.8 (CF$_3$), 104.3 (C-1'), 96.9 (C-1"), 87.4 (C-5), 79.3 (C-3), 78.3 (C-13), 77.3 (C-4"), 74.8 (C-11), 74.6 (C-6), 74.5 (C-12), 72.5 (C-3"), 70.5 (C-2'), 69.1 (C-5'), 65.8 (C-5"), 64.6 (C-3'), 62.1 (C-10), 49.1 (3"-OCH$_3$), 46.3 (C-2), 41.1 (C-4), 40.1 [3'-N(CH$_3$)$_2$], 34.7 (C-2"), 27.2 (C-4'), 28.8 (C-8), 24.0 (6-CH$_3$), 21.8 (C-14), 21.3 (8-CH$_3$), 20.7 (5'-CH$_3$), 21.1 (3"-CH$_3$), 17.6 (5"-CH$_3$), 17.0 (12-CH$_3$), 15.2 (2-CH$_3$), 13.2 (10-CH$_3$), 11.0 (15-CH$_3$), 9.8 (4-CH$_3$).

FAB-MS 922.4 [MH$^+$]

EXAMPLE 21

9-deoxo-9a-N-{N'-[(3-trifluoromethyl-phenyl)thiocarbamoyl]}-9a-aza-9a-homoerythromycin A From 9-deoxo-9a-aza-9a-homoerythromycin A (7.27 g; 0.00989 mole), 3-trifluoro-methylphenylisothiocyanate (2.64 g; 0.01299 mole) and toluene (40 ml) under stirring for 1 hour at room temperature and by evaporation of the reaction mixture under reduced pressure a crude product (9.27 g) was obtained. By crystallization from an acetone-petroleum ether mixture, from the crude product (1.0 g) the title product (0.6 g) having the following physico-chemical constants was obtained:

M.p. 110–112° C.

IR (KBr) cm$^{-1}$ 3454, 2975, 2938, 1734, 1599, 1531, 1494, 1453, 1378, 1331, 1252, 1166, 1124, 1093, 1051, 1012, 957, 904, 698.

$^1$H NMR (300 MHz, CDCl$_3$) δ 7.85–7.27 (Ph), 4.86 (H-1"), 4.81 (H-13), 4.43 (H-1'), 4.11 (H-3), 4.07 (H-5"), 3.51 (H-5'), 3.46 (H-5), 3.29 (3"-OCH$_3$), 3.25 (H-2'), 3.05 (H-9a), 3.04(H-4"), 2.80 (H-2), 2.58 (H-10), 2.45 (H-3'), 2.35 (H-2"a), 2.30 (3'-N(CH$_3$)$_2$), 1.84 (H-9b), 1.93 (H-4), 1.85 (H-14a), 1.75 (H-8), 1.67 (H-4'), 1.29, 1.55 (H-14b), 1.51 (H-2"b), 1.31 (6-CH$_3$), 1.29 (5"-CH$_3$), 1.23 (12-CH$_3$), 1.20(5'-CH$_3$), 1.20 (2-CH$_3$), 1.14 (10-CH$_3$), 1.09 (4-CH$_3$), 1.08 (3"-CH$_3$), 0.94 (8-CH$_3$), 0.92 (15-CH$_3$).

$^{13}$C NMR (75 MHz, CDCl$_3$) δ 183.3 (9a-NSONH), 177.9 (C-1), 140.4, 128.8, 125.7 123.6, 121.2 (Ph). 131.2, 130.7, 130.3, 129.9 (CF$_3$), 103.8 (C-1'), 94.9 (C-1"), 86.1 (C-5), 79.4 (C-3), 77.6 (C-4"), 70.5 (C-2'), 69.0 (C-5'), 65.5 (C-5"), 64.8 (C-3'), 56.8 (C-9), 56.6 (C-10). 49.2 (3"-OCH$_3$), 46.0 (C-2), 40.5 [3'-N(CH$_3$)$_2$], 34.6 (C-2"), 29.4 (C-8), 28.8 (C-4'), 21.7 (C-14), 21.3 (8-CH$_3$), 21.1 (5'-CH$_3$), 21.6 (3"-CH$_3$), 18.0 (5"-CH$_3$), 15.7 (12-CH$_3$), 14.8 (2-CH$_3$), 13.5 (10-CH$_3$), 11.0 (15-CH$_3$), 9.5 (4-CH$_3$).

FAB-MS 938.6 [MH$^+$]

EXAMPLE 22

9-deoxo-9a-N-{N'-[(2-trifluoromethoxy-phenyl)carbamoyl]}-9a-aza-9a-homoerythromycin A From 9-deoxo-9a-aza-9a-homoerythromycin A (1.5 g; 0.00204 mole), 2-trifluoro-methoxyphenylisocyanate (0.44 g; 0.00228 mole) and toluene (15 ml) under stirring for 3 hours at room temperature and by evaporation of the reaction mixture under reduced pressure a crude product (1.94 g) was obtained. By crystallization from an ethyl acetate-(n-hexane) mixture a chromatographically homogeneous product (1.39 g) having the following physico-chemical constants was obtained:

M.p. 126–128° C.

IR (KBr) cm$^{-1}$ 3466, 2974, 2938, 1732, 1669, 1610, 1531, 1455, 1380, 1315, 1250, 1217, 1169, 1109, 1094, 1054, 1013, 958, 897, 836, 758, 630.

FAB-MS 938.5 [MH$^+$]

EXAMPLE 23

9-deoxo-9a-N-{N'-[(4-tri fluoromethoxy-phenyl)thiocarbamoyl]}-9a-aza-9a-homoerythromycin A From 9-deoxo-9a-aza-9a-homoerythromycin A (1.5 g; 0.00204 mole), 4-trifluoro-methoxyphenylisothiocyanate (0.44 g; 0.00228 mole) and toluene (15 ml) under stirring for 2 hours at room temperature and by evaporation of the reaction mixture under reduced pressure a crude product (1.89 g) was obtained. By crystallization from an ethyl acetate-(n-hexane) mixture a chromatographically homogeneous product (1.15 g) having the following physico-chemical constants was obtained:

M.p. 139–141° C.

IR (KBr) cm$^{-1}$ 3456, 2975, 2940, 1731, 1669, 1511, 1457, 1414, 1380, 1265, 1199, 1166, 1111, 1054, 1015, 958, 897, 836.

FAB-MS 938.6 [MH$^+$]

What is claimed is:

1. A halo derivative of 9a-N-(N'-arylcarbamoyl) or 9a-N(N'-arylthiocarbamoyl)-9-deoxo-9a-aza-9a-homoerythromycin A of the general formula (I)

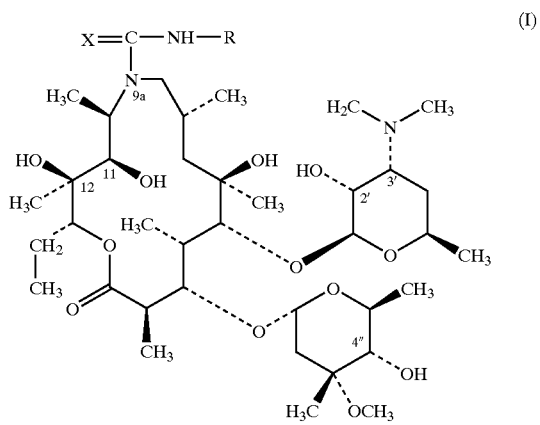

wherein R has the meaning of a substituted aryl group of the formula (II)

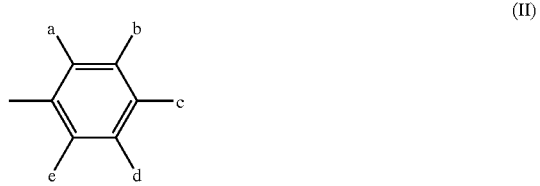

wherein substituents a, b, c, d and e are the same or different and at least one of them has the meaning of halo, a (C$_1$–C$_6$) haloalkyl or a (C$_1$–C$_6$) haloalkoxy group whereas the remaining ones have the meaning of hydrogen, halo, a (C$_1$–C$_6$) alkyl or a (C$_1$–C$_6$) alkoxy group, and X has the meaning of oxygen or sulfur or a pharmaceutically acceptable addition salt thereof by inorganic or organic acids.

2. A compound according to claim 1, characterized in that a has the meaning of halo, b, c, d and e ar the same and have the meaning of hydrogen and X is oxygen or sulfur.

3. A compound according to claim 2, characterized in that a has the meaning of fluoro and X is oxygen.

4. A compound according to claim 2, characterized in that a has the meaning of fluoro and X is sulfur.

5. A compound according to claim 2, characterized in that a has the meaning of chloro and X is sulfur.

6. A compound according to claim 1, characterized in that a has the meaning of halo, b, c and d are the same and have the meaning of hydrogen, e has the meaning of a (C$_1$–C$_4$) alkyl Group and X is oxygen or sulfur.

7. A compound according to claim 6, characterized in that a has the meaning of chloro, b, c and d are the same and have the meaning of hydrogen, e is methyl and X is oxygen.

8. A compound according to claim 1, characterized in that a, c, d and e are the same and have the meaning of hydrogen, b is halo and X is oxygen or sulfur.

9. A compound according to claim 8, characterized in that b has the meaning of fluoro and X is oxygen.

10. A compound according to claim 8, characterized in that b has the meaning of chloro and X is oxygen.

11. A compound according to claim 8, characterized in that b has the meaning of bromo and X is oxygen.

12. A compound according to claim 8, characterized in that b has the meaning of fluoro and X is sulfur.

13. A compound according to claim 8, characterized in that b has the meaning of chloro and X is sulfur.

14. A compound according to claim 8, characterized in that b has the meaning of bromo and X is sulfur.

15. A compound according to claim 1, characterized in that a, b, d and e are the some and have the meaning of hydrogen, c is halo and X is oxygen or sulfur.

16. A compound according to claim 15, characterized in that c has the meaning of chloro and X is oxygen.

17. A compound according to claim 15, characterized in that c has the meaning of bromo and X is oxygen.

18. A compound according to claim 15, characterized in that c has the meaning of chloro and X is sulfur.

19. A compound according to claim 15, characterized in that c has the meaning of bromo and X is sulfur.

20. A compound according to claim 1, characterized in that a, d and e are the same and have the meaning of hydrogen, b has the meaning of a ($C_1$–$C_6$) haloalkyl group, c is halo and X is oxygen or sulfur.

21. A compound according to claim 20, characterized in that a, d and e are the same and have the meaning of hydrogen, b is a —$CF_3$ group, c is chloro and X is oxygen.

22. A compound according to claim 1, characterized in that b, d and c are the same and have the meaning of hydrogen, a and c are the same and have the meaning of halo and X is oxygen or sulfur.

23. A compound according to claim 22, characterized in that a and c are the same and have the meaning of chloro and X is oxygen.

24. A compound according to claim 22, characterized that a and c are the same and have the meaning of chloro and X is sulfur.

25. A compound according to claim 1, characterized in that a, b, c, d and e are the same or different and have the meaning of hydrogen or of a ($C_1$–$C_4$) haloalkyl group and X is oxygen or sulfur.

26. A compound according to claim 25, characterized in that a is a —$CF_3$ group, b, c, d and e are the same and have the meaning of hydrogen and X is oxygen.

27. A compound according to claim 25, characterized in that a, c, d and e are td same and have the meaning of hydrogen, b is a —$CF_3$ group and X is oxygen.

28. A compound according to claim 25, characterized in that a, b, d and e are the same and have the meaning of hydrogen, c is a —$CF_3$ group and X is oxygen.

29. A compound according to claim 25, characterized in that a, c, d and e are the same and have the meaning of hydrogen, b is a —$CF_3$ group and X is sulfur.

30. A compound according to claim 1, characterized in that a, b, c, d and e are the same or different have the meaning of hydrogen or of a ($C_1$–$C_4$) haloalkoxy group and X is oxygen or sulfur.

31. A compound according to claim 30, characterized in that b, c, d and e are the same and have the meaning of hydrogen, a is a —$OCF_3$ group and X is oxygen.

32. A compound according to claim 30, characterized in that a, b, d and e are the same and have the meaning of hydrogen, C is a —$OCF_3$ group and X is oxygen.

33. Process for the preparation of halo derivative of 9a-N-(N'-arylcarbamoyl) or 9a-N-(N'-arylthiocarbamoyl)-9-deoxo-9a-aza-9a-homoerythromycin A of the general formula (I)

(I)

wherein R has the meaning of a substituted aryl group of the formula (II)

(II)

wherein substituents a, b, c, d and e are the same or different and at least one of them has the meaning of halo, a ($C_1$–$C_6$) haloalkyl or a ($C_1$–$C_6$) haloalkoxy group whereas the remaining ones have the of hydrogen, halo, a ($C_1$–$C_6$)alkyl or a ($C_1$–$C_6$) alkoxy group, and X has the meaning of oxygen or sulfur or a pharmaceutically acceptable addition salt thereof with inorganic or organic acids, characterized in that 9deoxo-9a-aza-9a-homoerythromycin A is subjected to a reaction with isocyanates or isothiocyanates of the general formula (III)

$$R-N=C=X \qquad (III)$$

wherein R and X have the above meanings, in an aprotic solvent, at room temperature or at elevated temperature.

34. A pharmaceutical composition, characterized in that it comprises a pharmaceutically acceptable carrier and an antibacterially effective amount of a compound according to claim 1.

35. A method for the treatment of bacterial infections which comprises administering to a patient in need thereof an effective amount of a compound according to claim 1.

36. The process of claim 33 wherein the aprotic solvent comprises toluene.

* * * * *